(12) United States Patent
Schreiber (10) Patent No.: US 11,559,263 B2
(45) Date of Patent: Jan. 24, 2023

(54) METHOD FOR IMPROVING THE IMAGE QUALITY OF X-RAY TOMOGRAMS

(71) Applicant: Siemens Healthcare GmbH, Erlangen (DE)

(72) Inventor: Bernd Schreiber, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 426 days.

(21) Appl. No.: 16/881,261

(22) Filed: May 22, 2020

(65) Prior Publication Data

US 2020/0367837 A1    Nov. 26, 2020

(30) Foreign Application Priority Data

May 22, 2019    (DE) .......................... 102019207504.5

(51) Int. Cl.
*A61B 6/03*     (2006.01)
*G06T 7/00*     (2017.01)
*H04N 5/32*     (2006.01)

(52) U.S. Cl.
CPC ............ *A61B 6/032* (2013.01); *G06T 7/0002* (2013.01); *H04N 5/32* (2013.01); *G06T 2207/10081* (2013.01)

(58) Field of Classification Search
CPC ..... A61B 6/032; A61B 6/4435; A61B 6/4441; A61B 6/03; A61B 6/5258; G06T 7/0002;

(Continued)

(56) References Cited

U.S. PATENT DOCUMENTS

2008/0056549 A1* 3/2008 Hamill ................. G06T 11/005
                                                                382/131
2010/0246917 A1* 9/2010 Bruder .................. A61B 6/482
                                                                382/131

(Continued)

OTHER PUBLICATIONS

Beatty, Jen, The Radon Transform and the Mathematics of Medical Imaging, published in 2012, pp. 1-26 (Year: 2012).*

(Continued)

*Primary Examiner* — Christine S. Kim
(74) *Attorney, Agent, or Firm* — Lempia Summerfield Katz LLC (57) ABSTRACT

A method for improving an image quality of X-ray tomograms includes generating a low-pass filtered X-ray tomogram by applying a low-pass filter to a two-dimensional X-ray tomogram. The low-pass filter is only applied to pixels with image values lying within a predetermined image value interval. A high-pass filtered X-ray tomogram is generated by subtracting the low-pass filtered X-ray tomogram from the two-dimensional X-ray tomogram. A Radon transform image is generated by calculating a Radon transform of the high-pass filtered X-ray tomogram. A modified Radon transform image is generated by modifying values of the pixels of the Radon transform image with values lying outside a predetermined value interval. A modified high-pass filtered X-ray tomogram is generated by calculating an inverse Radon transform of the modified Radon transform image. A modified X-ray tomogram is generated by the addition of the modified high-pass filtered X-ray tomogram to the low-pass filtered X-ray tomogram.

18 Claims, 6 Drawing Sheets

(58) Field of Classification Search
CPC ........ G06T 2207/10081; G06T 11/008; H04N 5/32
See application file for complete search history.

(56) References Cited

U.S. PATENT DOCUMENTS

2019/0139272 A1* 5/2019 Pan ...................... A61B 6/5258
2020/0196974 A1* 6/2020 Schreiber .............. G06T 11/008

OTHER PUBLICATIONS

Bal, Matthieu, and Lothar Spies. "Metal artifact reduction in CT using tissue-class modeling and adaptive prefiltering." Medical physics 33.8 (2006): 2852-2859.
Crawford, Carl R., et al. "High speed reprojection and its applications." Medical Imaging II. vol. 914. International Society for Optics and Photonics, 1988. pp. 1-9.
German Office Action for German Application No. DE 10 2019 207 504.5 dated May 22, 2020.
Mouton, Andre, et al. "An experimental survey of metal artefact reduction in computed tomography." Journal of X-ray Science and Technology 21.2 (2013): 193-226.
Wikipedia: "Radon-Transformation" Wikipedia-Extract; URL: https://de.wikipedia.org/w/index.php?title=Radon-Transformation&oldid=183179754; pp. 1-4 [Jan. 29, 2020].

* cited by examiner

METHOD FOR IMPROVING THE IMAGE QUALITY OF X-RAY TOMOGRAMS

This application claims the benefit of German Patent Application No. DE 10 2019 207 504.5, filed on May 22, 2019, which is hereby incorporated by reference in its entirety.

BACKGROUND

The present embodiments relate to improving an image quality of X-ray tomograms.

For a particularly detailed examination of an examination object (e.g., a patient and/or a workpiece and/or an examination phantom), frequently one or more two-dimensional projection images (e.g., X-ray projection images) are taken by an X-ray unit. Herein, a plurality of two-dimensional X-ray projection images, for example, may be recorded with different angulations to one another (e.g., projection angles) around a predetermined spatial axis. This may enable a three-dimensional reconstruction of a slice of the examination object. Herein, a two-dimensional X-ray tomogram may be generated by a suitable transform (e.g., an inverse Radon transform) of the plurality of two-dimensional projection images. The generation of such an X-ray tomogram may, for example, be enabled by a C-arm X-ray unit and/or a cone beam computed tomography system (cone beam CT) and/or a fan beam computed tomography system (fan beam CT) and/or an X-ray unit (e.g., a medical X-ray unit) including an X-ray source that is movable relative to the examination object and/or a detector that is movable relative to the examination object.

It is known from the prior art that streak artifacts (e.g., on the recording of two-dimensional X-ray tomograms) may occur. These streak artifacts frequently occur due to objects (e.g., radiopaque objects) inside and/or outside the examination object, which are arranged in the beam path between an X-ray source and an X-ray detector during the recording of the two-dimensional X-ray tomogram. Such objects may, for example, be catheters and/or cables and/or parts of a patient table and/or implants inside the examination object.

On the generation of an X-ray tomogram from a plurality of two-dimensional projection images with different projection angles, it may be the case, that, due to limited measuring times, not all projection regions (e.g., circular-segment-shaped projection regions) are completely covered. This may also result in the occurrence in streak artifacts in the X-ray tomogram.

Further, a movement of the examination object during the recording of the two-dimensional X-ray tomogram (e.g., over a lengthy period) may result in streak artifacts.

In addition, streak artifacts in the two-dimensional X-ray tomogram may be caused by arcing of the X-ray tube (e.g., the X-ray source). This may, for example, result in under-exposure of individual two-dimensional projection images, which may be used to generate the two-dimensional X-ray tomogram.

Streak artifacts (e.g., in different manifestations) may be conducive to misdiagnosis and/or mask low-contrast details of the examination object.

The methods known from prior art have the disadvantage that it is frequently not possible to correct streak artifacts (e.g., isolated occurrences of streak artifacts) in two-dimensional X-ray tomograms retrospectively.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method that enables the reduction of artifacts, such as isolated occurrences of streak artifacts, in X-ray tomograms, is provided.

Accordingly, it is provided that a low-pass filtered X-ray tomogram is generated by applying a low-pass filter (e.g., a non-linear low-pass filter) to a two-dimensional X-ray tomogram including a plurality of pixels. Herein, the low-pass filter is only applied to the pixels with image values lying within a predetermined image value interval. In addition, a high-pass filtered X-ray tomogram is generated by subtracting the low-pass filtered X-ray tomogram from the two-dimensional X-ray tomogram. The calculation of a Radon transform of the high-pass filtered X-ray tomogram generates a Radon transform image including a plurality of pixels. Further, the modification of values of the pixels of the Radon transform image with values lying outside a predetermined value interval generates a modified Radon transform image. The calculation of an inverse Radon transform of the modified Radon transform image enables the generation of a modified high-pass filtered X-ray tomogram. Subsequently, a modified X-ray tomogram is generated by adding the modified high-pass filtered X-ray tomogram to the low-pass filtered X-ray tomogram.

Herein, the two-dimensional X-ray tomogram may map a slice of the examination object (e.g., perpendicular to a spatial axis). In addition, the X-ray tomogram includes a plurality of pixels (e.g., image points) that in each case have a value (e.g., an image value; a gray value and/or an RGB color value and/or an intensity value).

The generation of the low-pass filtered X-ray tomogram and the high-pass filtered X-ray tomogram enables the X-ray tomogram to be divided into a high-frequency and a low-frequency component. Herein, low-contrast objects and high-contrast objects are retained in the low-pass filtered X-ray tomogram. This may, for example, be achieved in that the low-pass filter (e.g., the non-linear low-pass filter) is only applied to the pixels with image values lying within the predetermined image value interval (e.g., of low-contrast objects). As a result, the low-pass filtered X-ray tomogram may also contain all unfiltered pixels (e.g., high-contrast objects), to which the low-pass filter was not applied due to the respective image value. This enables it to be achieved that, on the subtraction of the low-pass filtered X-ray tomogram from the two-dimensional X-ray tomogram, the high-contrast objects contained therein and, for example, also the transitions and/or edges between low-contrast objects and high-contrast objects are removed from the high-pass filtered X-ray tomogram generated thereby.

Herein, low-contrast objects may, for example, be formed by soft tissue. High-contrast objects may, for example, be formed by sharp edges on transitions between different materials and/or at transitions between bone structures and soft tissue.

The high-pass filtered X-ray tomogram generated by subtracting the low-pass filtered X-ray tomogram from the two-dimensional X-ray tomogram may mostly have areas of quantum noise and/or structural noise and/or streak artifacts (e.g., in the soft-tissue component) of the X-ray tomogram.

This enables it to be provided that targeted treatment of streak artifacts may take place. The spatial resolution of the X-ray tomogram is not impaired, and/or the noise-power-spectrum remains unchanged. It is further possible for important (e.g., diagnostic) details (e.g., high-contrast objects) of the X-ray tomogram to be retained unchanged.

The non-linearity of the low-pass filter may enable a filtering (e.g., a weighted filtering) in dependence on the image value of the respective pixel and/or in dependence on a plurality of image values of pixels surrounding a pixel. Herein, an area of pixels within the respective X-ray tomogram may be determined, for example by applying a filter mask and/or by selecting a plurality of pixels arranged within a specified distance from a pixel. On the exemplary application of the non-linear low-pass filter, it is, for example, possible for a comparison value (e.g., a difference and/or a quotient and/or a sum and/or a product) of the image value of the pixel with a plurality of image values of pixels surrounding a pixel to be formed. The filtering (e.g., weighted filtering) may take place in dependence on the comparison value.

This enables it to be provided that details (e.g., diagnostic details) in the respective X-ray tomogram are still retained after the application of the low-pass filter. Herein, the details considered in the respective X-ray tomogram are, for example, edges and/or transitions between different contrast objects in the X-ray tomogram.

On the calculation of the Radon transform of the high-pass filtered X-ray tomogram, in each case, for example, a line integral is determined along all straight lines in a plane inside the X-ray tomogram. Hereinafter, these straight lines are referred to as Radon transform straight lines. Herein, a Radon transform image including a plurality of pixels is generated. The values of the plurality of pixels is low (e.g., close or equal to zero). Due to the fact that the high-pass filtered X-ray tomogram to which the Radon transform is applied may mostly have areas of quantum noise and/or structural noise and/or streak artifacts, the nature of the quantum noise and/or the structural noise provides that constructive interference of a plurality of image values of pixels along a straight line parallel to a projection direction inside the high-pass filtered X-ray tomogram may only occur in the presence of streak artifacts. Herein, the projection direction may be perpendicular to the Radon transform straight line along which the line integral is determined.

For example, it is only on constructive interference of a plurality of image values of pixels along a straight line parallel to the projection direction inside the high-pass filtered X-ray tomogram that a high quantity for the values of the pixel assigned in each case forms in the Radon transform image generated therefrom. If no constructive interference of a plurality of image values of pixels along a straight line parallel to the projection direction occurs inside the high-pass filtered X-ray tomogram, a lower quantity for the value of the pixel assigned in each case forms in the Radon transform image generated therefrom. Hence, the quantities for the values of the pixels of the Radon transform image may be used to infer whether the high-pass filtered X-ray tomogram contains a streak artifact or noise along the straight line assigned to the respective pixel parallel to the projection direction extending perpendicular to the Radon transform straight line.

Part of the suggested method according to the present embodiments entails the performance of a comparison with a predetermined value interval for all the values of the pixels of the Radon transform image in each case. Herein, the predetermined value interval may, for example, on a consideration of the quantities for the values of the pixels of the Radon transform image, include all values between zero and an upper threshold value. If the comparison reveals that the value of a pixel of the Radon transform image lies outside the predetermined value interval, the value of the pixel is modified. Herein, the modification of the value of the pixel may, for example, include a substitution according to a mapping specification and/or a scaling.

The comparison of the values of the pixels of the Radon transform image with the predetermined value interval, for example, enables a modification of the values of the pixels that correspond to a straight line parallel to the projection direction of the Radon transform along which constructive interference (e.g., due to a streak artifact) is present. Herein, the modified Radon transform image is generated. Hence, it is advantageous for the value interval to be predetermined such that values of pixels from constructive interference of the Radon transform lie outside the value interval.

A subsequent calculation of the inverse Radon transform of the modified Radon transform image generates a modified high-pass filtered X-ray tomogram. Ideally, streak artifacts that may, for example, be contained in the high-pass filtered X-ray tomogram are not contained in the modified high-pass filtered X-ray tomogram.

The modified X-ray tomogram, which is generated by adding the modified high-pass filtered X-ray tomogram to the low-pass filtered X-ray tomogram, may contain all the low-contrast objects and/or high-contrast objects from the X-ray tomogram, but, for example, no streak artifacts.

In a further embodiment, the two-dimensional X-ray tomogram may be reconstructed from a plurality of two-dimensional projection images with at least partially different projection angles. Herein, the plurality of two-dimensional projection images may, for example, be recorded by cone beam projection and/or fan beam projection.

Herein, the X-ray tomogram may, for example, be generated by a computed tomography system and/or a C-arm X-ray unit. On the reconstruction of the X-ray tomogram from the plurality of two-dimensional projection images with at least partially different projection angles, it is, for example, possible to apply an inverse Radon transform.

Application of the suggested method is advantageous for X-ray tomograms generated in this way since incomplete coverage of all the projection regions (e.g., circular projection regions) may result in the formation of streak artifacts in the X-ray tomogram.

In a further embodiment, the predetermined image value interval may be specified for a value range of soft tissue. Herein, the predetermined image value interval for the value range of the soft tissue may, for example, include image values of muscular tissue and/or connective tissue and/or adipose tissue. Image values of metallic objects and/or contrast agents and/or bone structures and/or blood vessels and/or nerves and/or air may not be contained in the predetermined image value interval. As a result, it may be provided that, for example, diagnostic details in the X-ray tomogram are retained in the modified X-ray tomogram following the application of an embodiment of the method according to the present embodiments.

In a further embodiment, to calculate the Radon transform, an interpolation may be applied to the high-pass filtered X-ray tomogram (e.g., by a Kaiser-Bessel function). Alternatively or additionally thereto, to calculate the inverse Radon transform, an interpolation may be applied to the modified Radon transform image (e.g., by a Kaiser-Bessel function). This enables a reduction of the spatial resolution on the application of the Radon transform to the high-pass filtered X-ray tomogram and/or on the application of the inverse Radon transform to the modified Radon transform image to be avoided.

The calculation of the Radon transform and/or the inverse Radon transform frequently requires pixels to be transformed from a Radon polar coordinate system into a Cartesian coordinate system or vice versa. Herein, suitable interpolation (e.g., by the Kaiser-Bessel function) may enable improved mapping between the Radon polar coordinate system and the Cartesian coordinate system.

In a further embodiment, a multiple (e.g., integral) of a standard deviation of the values of the pixels of the Radon transform image may be specified as the predetermined value interval for the generation of the modified Radon transform image. For example, in the case of only isolated occurrences of streak artifacts in the X-ray tomogram, the pixels of the Radon transform image mostly have low-quantity values. In the exemplary embodiment suggested herein, an integral multiple of the standard deviation of the values of the pixels of the Radon transform image in the predetermined value interval is specified (e.g., as a lower and/or upper threshold value). If the quantities for the values of the pixels of the Radon transform image are taken into account in the comparison with the predetermined value interval, it is, for example, possible to determine a value of zero or close to zero as the lower threshold value and an integral multiple of the standard deviation of the values of the pixels of the Radon transform image as the upper threshold value.

This enables it to be provided that the majority of pixels of the Radon transform image lie inside the predetermined value interval so that the values of these pixels are not modified. Hence, the few pixels of the Radon transform image with a quantity for the value that is, for example, higher than the majority of the other pixels may be identified over the predetermined value interval and subsequently modified.

In a further embodiment, on the modification of the values of the pixels of the Radon transform image, the values lying outside a predetermined value interval are set to zero. This enables it to be achieved that values of pixels corresponding to a straight line parallel to the projection direction of the Radon transform along which a constructive interference is present are set to zero. Hence, in other words, values of pixels of the Radon transform image corresponding to a streak artifact in the high-pass filtered X-ray tomogram may be set to zero. The application of the inverse Radon transform applied to the modified Radon transform image causes modified (e.g., zeroed) values of the pixel to be transformed into a plurality of pixels of the modified X-ray tomogram. This enables possible streak artifacts of the X-ray tomogram to be removed in an effective and particularly reliable manner.

In a further embodiment, values of pixels of the Radon transform image arranged within a specified distance from a pixel with a value outside the predetermined value interval may be modified. For example, partial volume effects on the recording and/or generation of the X-ray tomogram may cause streak artifacts, at least partially, also to be contained in pixels outside a straight line parallel to the projection direction along which the streak artifact extends. According to an embodiment of the method, on the application of the Radon transform to the high-pass filtered X-ray tomogram, this may have the result that pixels within a specific distance from a pixel with a value outside the predetermined value interval correspond at least partially to a streak artifact in the X-ray tomogram. Herein, the values of the pixel within a specified distance from a pixel with a value outside the predetermined value interval may be modified (e.g., with weighting). This also enables it to be provided that no at least partial streak artifacts due to partial volume effects may occur in the modified X-ray tomogram.

In a further embodiment, the values of the pixels of the Radon transform image arranged within a specified distance from a pixel with a value outside the predetermined value interval may be modified in dependence on the distance to the pixel with the value outside the predetermined value interval. This may, for example, enable weighted modification of the value of the pixels in dependence on the distance. This may, for example, be advantageous for taking better account of partial volume effects of the streak artifacts.

In a further embodiment, the values of pixels of the Radon transform image arranged within a specified distance from a pixel with a value outside the predetermined value interval are set to zero. If the X-ray tomogram has one or more streak artifacts, this may enable particularly reliable removal of the streak artifacts, for example, also taking account of partial volume effects within the pixels of the X-ray tomogram.

In a further embodiment, the low-pass filter may include a median filter and/or a bilateral filter (e.g., one or more weighted filters). It is known from the prior art that streak artifacts in X-ray tomograms frequently only have a low difference in contrast compared to low-contrast objects (e.g., soft tissue). For better separation of pixels of the X-ray tomogram corresponding to a streak artifact and pixels of the X-ray tomogram which, for example, correspond to a low-contrast object, a median filter and/or a bilateral filter (e.g., one or more weighted filters) may be applied. This enables it to be provided that the low-pass filtered X-ray tomogram has no, or only very low, streak artifact components.

In a further embodiment, application (e.g., slice-by-slice application) of the suggested method to a three-dimensional original data record including a plurality of two-dimensional X-ray tomograms enables a modified three-dimensional data record to be generated. Herein, the three-dimensional original data record may include a plurality of X-ray tomograms (e.g., sectional X-ray images) and/or may be separated into a plurality of X-ray tomograms along a predetermined spatial dimension. Herein, the application of an embodiment of the method may, for example, take place in a three-dimensional and/or two-dimensional manner. In the case of the two-dimensional application of the suggested method, it is possible (e.g., based on the plurality of two-dimensional X-ray tomograms of the three-dimensional original data record) for a plurality of modified X-ray tomograms to be generated. The plurality of modified X-ray tomograms may be combined to form a modified three-dimensional data record. Herein, it is, for example, also possible only to apply the suggested method to a subset of all the two-dimensional X-ray tomograms contained in the three-dimensional original data record. This enables the computing effort for carrying out the suggested method to be reduced.

In addition, one embodiment of the method may include the direct application of individual elements of the method (e.g., the low-pass filter and/or Radon transform and/or the inverse Radon transform) to three-dimensional X-ray images. Herein, it is also possible, for example, to include regions of pixels adjacent to a slice of pixels of the three-dimensional original data record in the filtering.

Further suggested is an X-ray unit (e.g., a medical X-ray unit) that is configured to carry out a method for improving the image quality of X-ray tomograms (e.g., medical X-ray tomograms). Such an X-ray unit (e.g., medical X-ray unit) may, for example, be embodied as a C-arm X-ray unit and/or as a computed tomography (CT) system. The X-ray unit is further embodied to generate a low-pass filtered X-ray tomogram by applying a low-pass filter (e.g., a non-linear low-pass filter) to a two-dimensional X-ray tomogram including a plurality of pixels. Herein, the low-pass filter is only applied to the pixels with image values lying within a predetermined image value interval. Moreover, a high-pass filtered X-ray tomogram is generated by subtracting the low-pass filtered X-ray tomogram from the two-dimensional X-ray tomogram. In addition, a Radon transform image including a plurality of pixels is generated by calculating a Radon transform of the high-pass filtered X-ray tomogram. Further, modification of the values of the pixels of the Radon transform image with values lying outside a predetermined value interval generates a modified Radon transform image. Moreover, the calculation of an inverse Radon transform of the modified Radon transform image generates a modified high-pass filtered projection image. After this, a modified X-ray tomogram is generated by adding the modified high-pass filtered X-ray tomogram to the low-pass filtered X-ray tomogram.

Further suggested is a processing unit (e.g., a microprocessor) configured to process information and/or data and/or signals from the X-ray unit and/or further components. The processing unit is further configured to send control commands to the X-ray unit and/or constituent parts of the X-ray unit and/or further components.

The X-ray unit may, for example, include a depiction unit (e.g., a display and/or a monitor) configured to display information and/or graphical representations of information of the X-ray unit and/or further components.

The advantages of the suggested X-ray unit substantially correspond to the advantages of the suggested method for improving the image quality of X-ray tomograms (e.g., medical X-ray tomograms). Features, advantages, or alternative embodiments may also be transferred to the other matter and vice versa.

Further provided is a computer program product that includes a program and may be loaded directly into a memory of a programmable computing unit and includes program means (e.g., libraries and auxiliary functions) in order to carry out a method for improving the image quality of X-ray tomograms when the computer program product is executed. Herein, the computer program product may include software with a source code that still has to be compiled and linked or only has to be interpreted, or an executable software code that still only has to be loaded into the processing unit for execution. The computer program product enables the method for improving the image quality of X-ray tomograms to be carried out quickly, identically repeatably, and robustly. The computer program product is configured to carry out the method acts according to the present embodiments by the processing unit. Herein, the processing unit is in each case to fulfill the requisite conditions such as, for example, having an appropriate random access memory, an appropriate graphics card, or an appropriate logic unit so that the respective may be carried out efficiently.

The computer program product is, for example, stored on a computer-readable medium or held resident on a network or server from where the computer program product may be loaded into the processor of a processing unit that is directly connected to the processing unit or may be embodied as part of the processing unit. Control information of the computer program product may be stored on an electronically readable data carrier (e.g., a non-transitory computer-readable storage medium). The control information of the electronically readable data carrier may be configured to carry out a method according to the present embodiments when the data carrier is used in a processing unit. Examples of electronically readable data carriers include a DVD, a magnetic tape, or a USB stick on which electronically readable control information (e.g., software) is stored. When this control information is read from the data carrier and stored in a processing unit, all embodiments of the above-described method may be carried out. For example, the present embodiments may also be based on the computer-readable medium and/or the electronically readable data carrier.

BRIEF DESCRIPTION OF THE DRAWINGS

Exemplary embodiments of the invention are depicted in the drawings and described in more detail below. The same reference characters are used for the same features in the different figures, which show.

DETAILED DESCRIPTION

Figure 1:
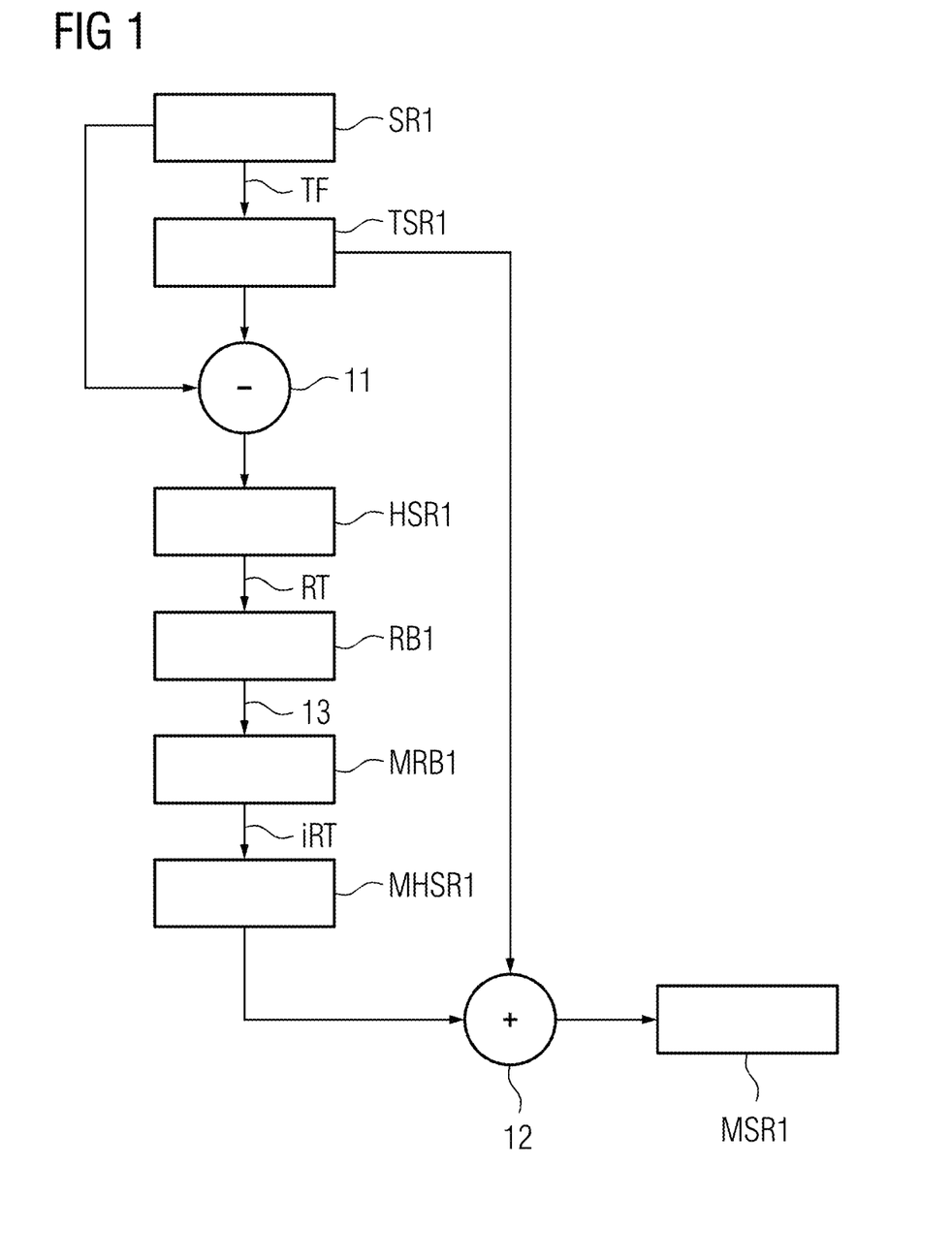
FIG. 1 is a schematic depiction of an embodiment of a method.

FIG. 1 is a schematic depiction of an embodiment of a method. In a first act, a low-pass filtered X-ray tomogram TSR1 is generated by applying a low-pass filter TF (e.g., a non-linear low-pass filter) to a two-dimensional X-ray tomogram SR1 including a plurality of pixels. Herein the low-pass filter TF is only applied to the pixels of the two-dimensional X-ray tomogram SR1 with image values lying within a predetermined image value interval.

Herein, the two-dimensional X-ray tomogram SR1 may be generated from a plurality of two-dimensional projection images with at least partially different projection angles. Herein, the plurality of two-dimensional projection images may, for example, be recorded by cone beam projection.

The predetermined image value interval may be specified for a value range of soft tissue (e.g., muscle tissue and/or connective tissue and/or adipose tissue). The low-pass filter TF may further include a median filter and/or a bilateral filter (e.g., one or more weighted filters). This also enables pixels that are arranged in the spatial vicinity of a pixel with a value lying within the predetermined image value interval to be included in the filtering.

In a further act, a high-pass filtered X-ray tomogram HSR1 may be generated by subtracting 11 the low-pass filtered X-ray tomogram TSR1 from the two-dimensional X-ray tomogram SR1.

The calculation of a Radon transform RT of the high-pass filtered X-ray tomogram HSR1 enables the generation of a Radon transform image RB1 including a plurality of pixels. The modification 13 of values of the pixels of the Radon transform image RB1 with values lying outside a predetermined value interval enables the generation of a modified Radon transform image MRB1. After this, the calculation of an inverse Radon transform iRT of the modified Radon transform image MRB1 enables the generation of a modified high-pass filtered X-ray tomogram MHSR1.

For example, to calculate the Radon transform RT and/or the inverse Radon transform iRT, an interpolation may be applied (e.g., by a Kaiser-Bessel function) to the high-pass filtered X-ray tomogram HSR1.

On the modification of the values of the pixels of the Radon transform image RB1, the values lying outside the predetermined value interval are set to zero.

In addition, the values of the pixels of the Radon transform image RB1 arranged within a specified distance (e.g., a radius) from a pixel with a value outside the predetermined value interval may be modified. Herein, the values of the pixels of the Radon transform image RB1 arranged within a specified distance from a pixel with a value outside the predetermined value interval are set to zero. Alternatively or additionally thereto, the modification may, for example, take place in dependence on the distance from the pixel with the value outside the predetermined value interval.

The addition 12 of the modified high-pass filtered X-ray tomogram MHSR1 to the low-pass filtered X-ray tomogram TSR1 enables the generation of a modified X-ray tomogram MSR1.

An embodiment of the method may also include the generation of a modified three-dimensional data record, where this may be generated by the application (e.g., slice-by-slice application) of the method depicted in FIG. 1 to a three-dimensional original data record including a plurality of two-dimensional X-ray tomograms.

Figure 2:
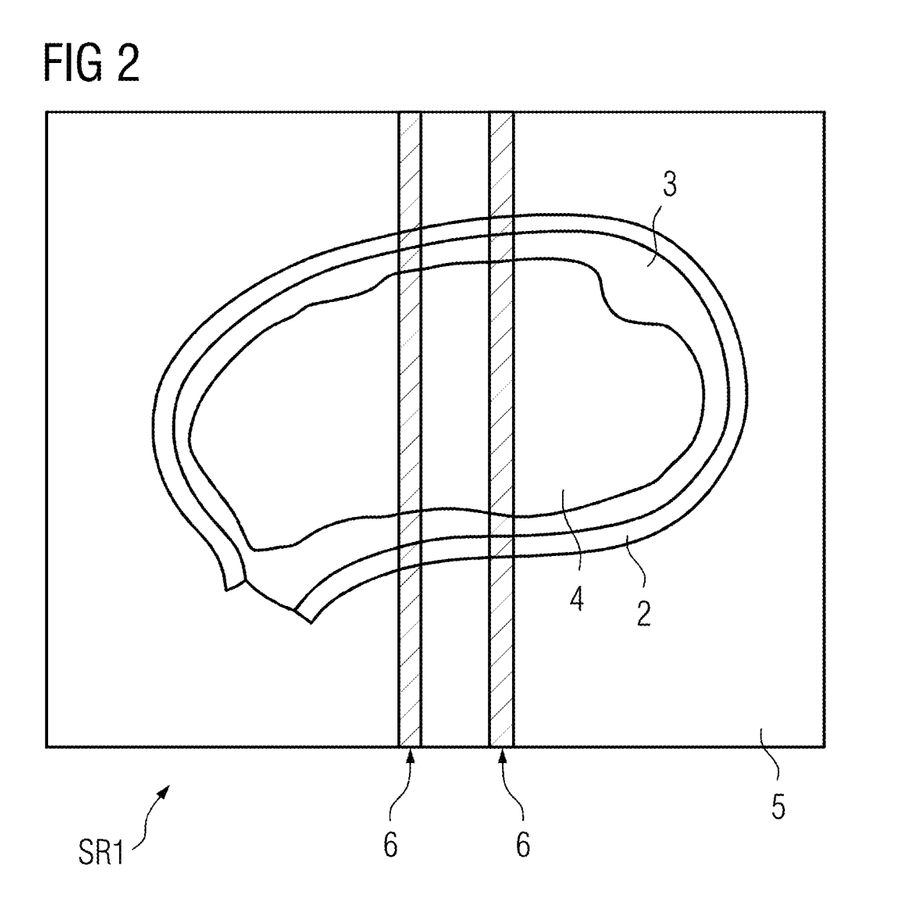
FIG. 2 is a schematic depiction of an exemplary X-ray tomogram with an anatomical structure and streak artifacts.

FIG. 2 is a schematic depiction mapping a two-dimensional X-ray tomogram SR1 with an anatomical structure and streak artifacts 6. Herein, the schematically depicted anatomical structure may include different contrast objects (e.g., low-contrast objects and/or high-contrast objects). In the present exemplary embodiment, the anatomical structure includes a cranial bone 2, an area 3 filled with, for example, cerebrospinal, fluid, and a soft tissue 4 (e.g., a white brain substance and/or gray brain substance). The two-dimensional X-ray tomogram SR1 may, for example, in a background of the two-dimensional X-ray tomogram SR1, have an area 5 of quantum noise and/or structural noise. The two-dimensional X-ray tomogram SR1 may also have one or more streak artifacts 6 (e.g., along one or more directions).

Figure 3:
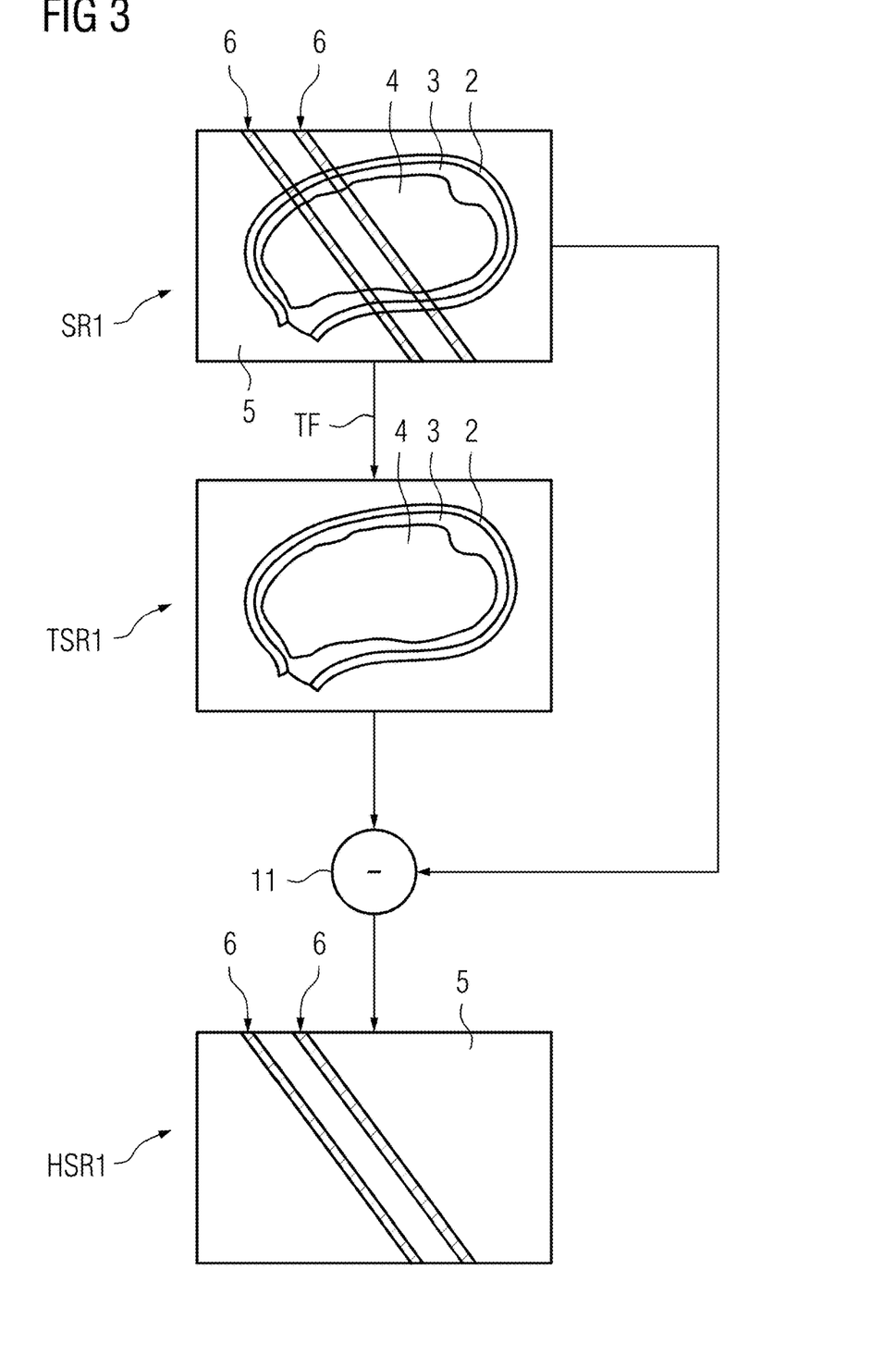
FIG. 3 is a schematic depiction of an application of a part of an embodiment of the method to an X-ray tomogram with streak artifacts.

FIG. 3 is a schematic depiction of an application of a part of an embodiment of the method to the two-dimensional X-ray tomogram SR1 with an anatomical structure and streak artifacts 6. Following the application of the low-pass filter TF to the pixels of the two-dimensional X-ray tomogram SR1 with image values lying within a predetermined image value interval, the low-pass filtered X-ray tomogram TSR1 may be generated.

Herein, the application of the low-pass filter TF to the two-dimensional X-ray tomogram SR1 advantageously causes the anatomical structure, which includes the cranial bone 2, the cerebrospinal fluid 3, and the soft tissue 4, to be retained in the low-pass filtered X-ray tomogram TSR1. Herein, the low-pass filtered X-ray tomogram TSR1 may also include all unfiltered pixels to which the low-pass filter TF was not applied due to the respective image value. This enables it to be provided that, on the subtraction 11 of the low-pass filtered X-ray tomogram TSR1 from the two-dimensional X-ray tomogram SR1, the high-contrast objects contained therein (e.g., the cranial bone 2) and the transitions and/or edges between low-contrast objects (e.g., the soft tissue 4) and high-contrast objects are also removed from the high-pass filtered X-ray tomogram HSR1 generated herein.

The high-pass filtered X-ray tomogram HSR1 advantageously includes the streak artifacts 6 and an area 5 of quantum noise and/or structural noise.

Figure 4:
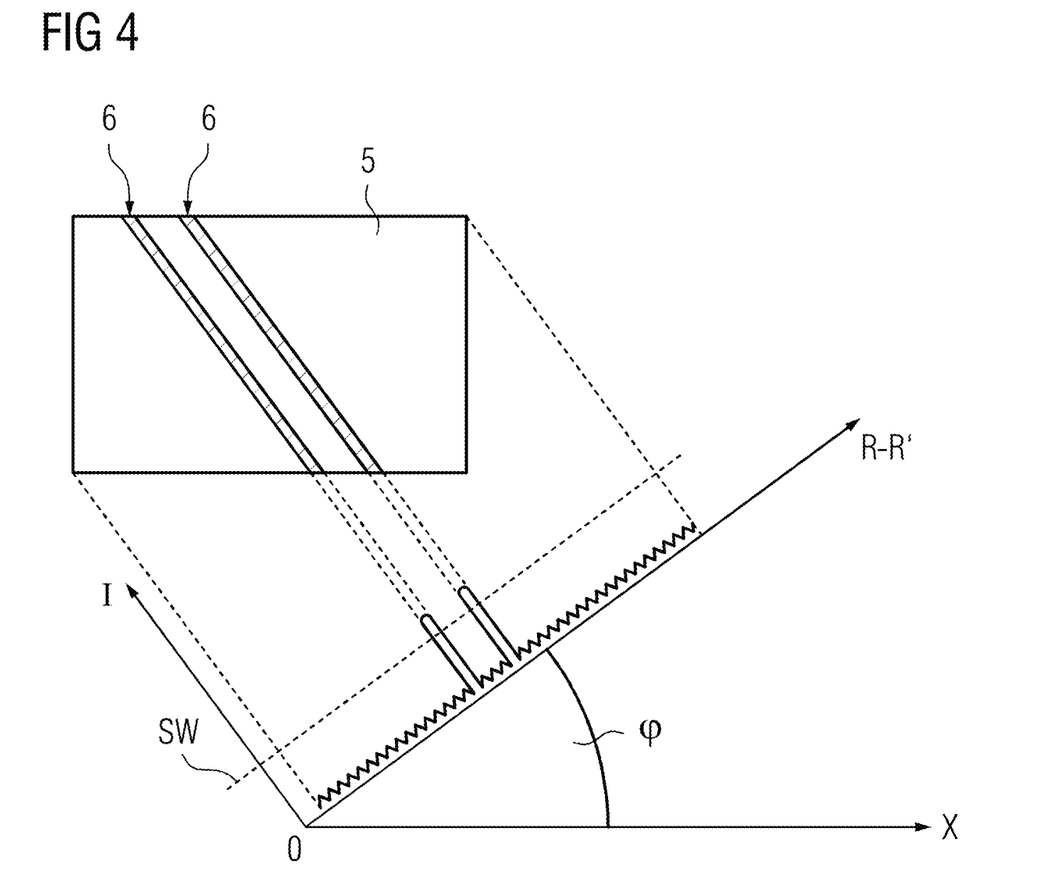
FIG. 4 is a schematic depiction of a Radon transform of a high-pass filtered X-ray tomogram with streak artifacts.

FIG. 4 is a schematic depiction mapping a Radon transform RT of a high-pass filtered X-ray tomogram HSR1 with streak artifacts 6. Herein, for example, a line integral I is determined along the straight line R-R'. Herein, the straight line R-R' has an angle φ to an axis x of the high-pass filtered X-ray tomogram HSR1. On the integration of the values of the pixel of the high-pass filtered X-ray tomogram HSR1 along a straight line parallel to the projection direction and perpendicular to the straight line R-R', constructive interference, for example, occurs along the streak artifacts 6.

The high-pass filtered X-ray tomogram HSR1 may include mostly areas 5 of quantum noise and/or structural noise and/or streak artifacts 6. Due to the nature of the quantum noise and/or the structural noise, constructive interference of a plurality of image values of pixels of the high-pass filtered X-ray tomogram HSR1 on projection onto the straight line R-R' may only occur in the presence of streak artifacts 6. In the case of such constructive interference, a higher quantity for the value of the pixel assigned in each case forms at the position of the line integral I corresponding to the intersection of the straight line parallel to the projection direction with the straight line R-R'. If no constructive interference occurs, a lower quantity for the value of the pixel assigned in case forms at the position of the line integral I corresponding thereto. Hence, the quantities for the values of the pixels of the Radon transform image RB1 may be used to infer whether the high-pass filtered X-ray tomogram HSR1 contains a streak artifact or noise along the straight line assigned to the respective pixel parallel to the projection direction extending perpendicular to the Radon transform straight line R-R'.

In order to generate the modified Radon transform image MRB1, the values of the pixels of the Radon transform image RB1 are compared with a predetermined value interval. If the quantities for the values of the pixels of the Radon transform image RB1 are taken into account for this comparison, the predetermined value interval may include a value of zero as a lower threshold value and an upper threshold value SW.

Consequently, the pixels of the Radon transform image RB1 with a value outside the predetermined value interval (e.g., above the upper threshold value SW) may be identified as the result of constructive interference along the assigned straight line parallel to the projection direction of the Radon transform RT. This enables a particularly simple and reliable identification of the streak artifacts 6 in the high-pass filtered X-ray tomogram HSR1.

Further, a multiple (e.g., an integral) of a standard deviation of the values of the pixels of the Radon transform image RB1 may be specified as the predetermined value interval.

Figure 5:
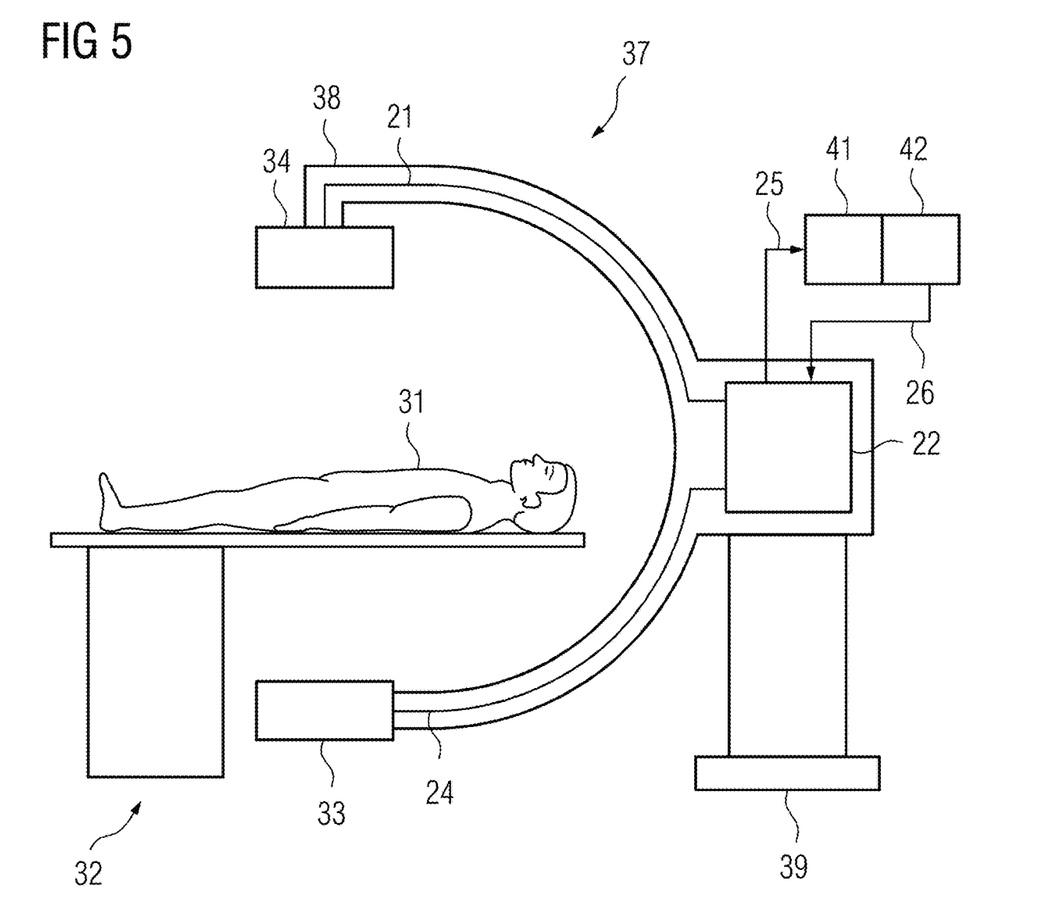
FIG. 5 is a schematic depiction of one embodiment of a medical C-arm X-ray unit.

FIG. 5 shows a schematic depiction of one embodiment of a medical C-arm X-ray unit 37 that is configured to carry out an embodiment of the method. Herein, the medical C-arm X-ray unit 37 includes a detector unit 34, an X-ray source 33, and a processing unit 22. In order to record a two-dimensional X-ray tomogram SR1 and/or a three-dimensional original data record including a plurality of two-dimensional X-ray tomograms, the arm 38 of the C-arm X-ray unit may be mounted movably about one or more axes. This, for example, enables a plurality of two-dimensional projection images with at least partially different projection angles to be recorded, where the two-dimensional X-ray tomogram SR1 may be reconstructed from the plurality of two-dimensional projection images. The medical C-arm X-ray unit 37 may further include a moving apparatus 39 that enables movement of the C-arm X-ray unit 37 in space.

In order to record a two-dimensional X-ray tomogram SR1 of a region to be imaged of an examination object 31 arranged on a patient mounting device 32, the processing unit 22 may send a signal 24 to the X-ray source 33. Following this, the X-ray source 33 may send an X-ray beam (e.g., a cone beam and/or a fan beam). When, after interaction with the region of the examination object 31 to be depicted, the X-ray beam arrives at a surface of the detector unit 34, the detector unit 34 may send a signal 21 to the processing unit 22. The processing unit 22 may, for example, use the signal 21 to generate a two-dimensional X-ray tomogram SR1. Subsequently, the processing unit 22 may carry out an embodiment of the method for improving the image quality of X-ray tomograms. Herein, it is possible for a modified X-ray tomogram MSR1 to be generated.

In addition, the medical C-arm X-ray unit 37 may include an input unit 41 (e.g., a keyboard) and/or a depiction unit 42 (e.g., a monitor and/or a display). The input unit 41 may be integrated in the depiction unit 42 (e.g., in the case of a capacitive input display). Herein, an entry by an operator at the input unit 41 may enable the suggested method to be controlled.

Figure 6:
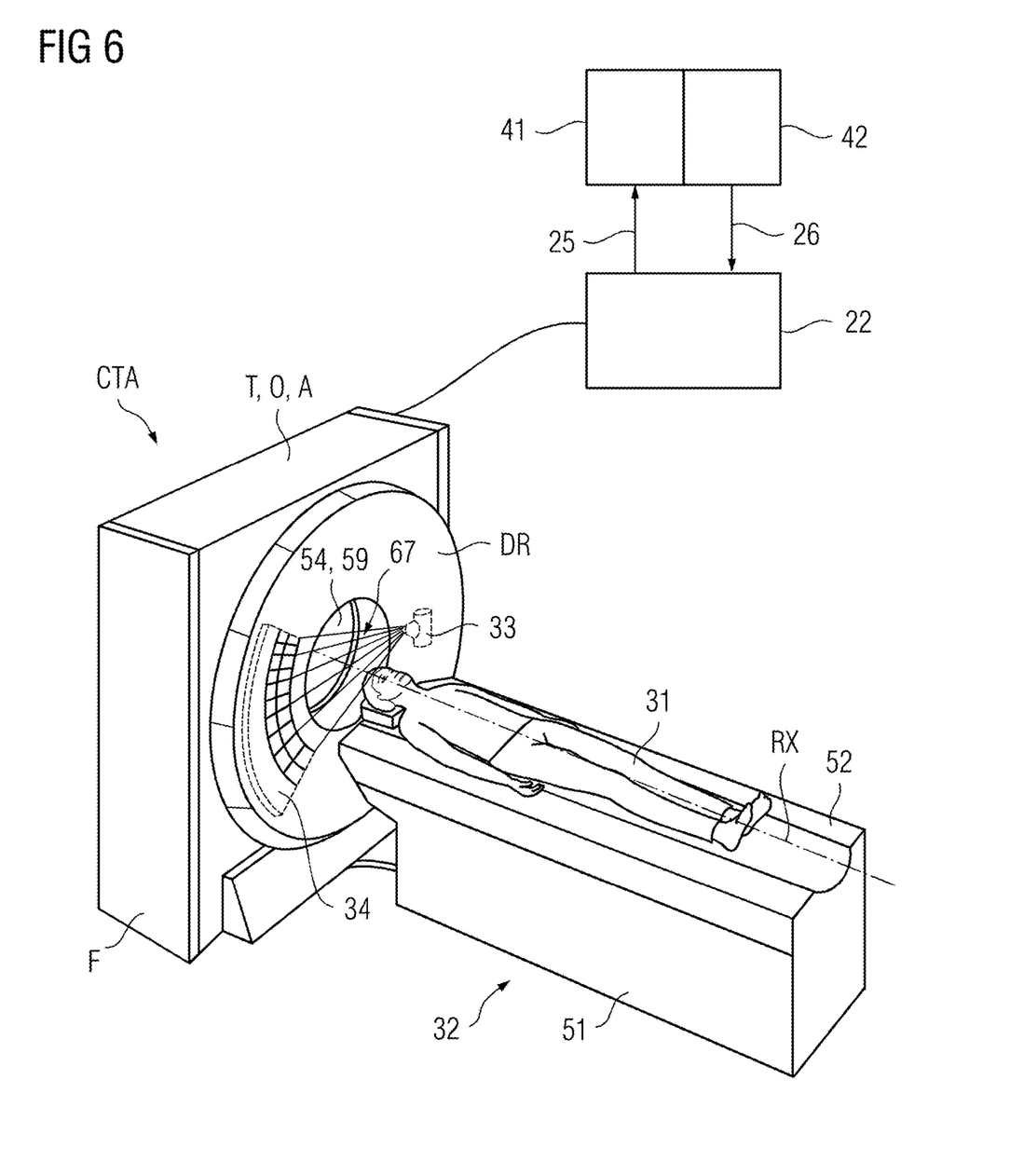
FIG. 6 is a schematic depiction of one embodiment of a medical computed tomography system.

FIG. 6 is a schematic depiction of a medical computed tomography system CTA that is configured to carry out an embodiment of the method. The computed tomography system CTA has an X-ray source 33, a detector unit 34, a cover A, a support frame F, a rotating frame DR, and a rotary bearing. The support frame F, the rotating frame DR, and the rotary bearing are surrounded by the cover A and hence are located in a cavity bounded by the cover A.

The X-ray source 33 and the detector unit 34 are arranged opposite one another relative to an axis of rotation RX on the rotating frame DR, where the rotating frame DR is connected to an annular frame O by the rotary bearing such that the rotating frame DR is rotatably mounted about the axis of rotation RX relative to the annular frame O.

The examination object 1 may be introduced into the tunnel-shaped opening 59. The acquisition region 54 is located in the tunnel-shaped opening 59. A region of the examination object 31 to be mapped may be positioned in the acquisition region 54 such that an X-ray beam 67 (e.g., a cone beam and/or fan beam) may travel from the X-ray source 33 to the region to be mapped and, following interaction with the region to be mapped, arrive at the detector unit 34.

The patient mounting device 32 may have a mounting base 51 and a mounting plate 52 for mounting the examination object 31. The mounting plate 52 is arranged movably relative to the mounting base 51 on the mounting base 51 such that the mounting plate 52 may be introduced into the acquisition region 54 in a longitudinal direction of the mounting plate 52.

The X-ray source 33 is arranged on the rotating frame DR and embodied to emit an X-ray beam 67. The detector unit 34 is arranged on the rotating frame DR embodied to detect the X-ray beam 67. The X-ray beam 67 may travel from the X-ray source 33 to the region of the examination object 31 to be depicted and, following interaction with the region to be depicted, arrive at a surface of the detector unit 34. The computed tomography system CTA further has a processing unit 22, a depiction unit 42, and an input unit 43.

The processing unit 22 may, for example, generate a two-dimensional tomogram SR1 using a signal from the detector unit 34. Subsequently, the processing unit 22 may carry out an embodiment of the method for improving the image quality of X-ray tomograms. Herein, i a modified X-ray tomogram MSR1 may be generated.

The schematic depictions in the figures described do not illustrate a scale or size relationship.

Reference is made once again to the fact that the method devices described in detail above and the device depicted are only exemplary embodiments that may be varied in wide ranges by the person skilled in the art without departing from the scope of the invention. The use of the indefinite article "a" or "an" does not preclude the possibility that the features in question may also be present on a multiple basis. Similarly, the term "unit" does not preclude the possibility that the components in question may consist of a plurality of interacting part-components, which, if necessary, may also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for improving an image quality of X-ray tomograms, the method comprising:
    generating a low-pass filtered X-ray tomogram, the generating of the low-pass filtered X-ray tomogram comprising applying a low-pass filter to a two-dimensional X-ray tomogram comprising a plurality of pixels, wherein the low-pass filter is only applied to pixels of the plurality of pixels with image values lying within a predetermined image value interval;
    generating a high-pass filtered X-ray tomogram, the generating of the high-pass filtered X-ray tomogram comprising subtracting the low-pass filtered X-ray tomogram from the two-dimensional X-ray tomogram;
    generating a Radon transform image comprising a plurality of pixels, the generating of the Radon transform image comprising calculating a Radon transform of the high-pass filtered X-ray tomogram;
    generating a modified Radon transform image, the generating of the modified Radon transform image comprising modifying values of the pixels of the Radon transform image with values lying outside a predetermined value interval;
    generating a modified high-pass filtered X-ray tomogram, the generating of the modified high-pass filtered X-ray tomogram comprising calculating an inverse Radon transform of the modified Radon transform image; and
    generating a modified X-ray tomogram, the generating of the modified X-ray tomogram comprising adding the modified high-pass filtered X-ray tomogram to the low-pass filtered X-ray tomogram.

2. The method of claim 1, wherein the two-dimensional X-ray tomogram is reconstructed from a plurality of two-dimensional projection images with at least partially different projection angles.

3. The method of claim 1, wherein the predetermined image value interval is specified for a value range of soft-tissue.

4. The method of claim 1, wherein calculating the Radon transform comprises applying an interpolation to the high-pass filtered X-ray tomogram.

5. The method of claim 1, wherein calculating the inverse Radon transform comprises applying an interpolation to the modified Radon transform image.

6. The method of claim 1, wherein a multiple of a standard deviation of the values of the pixels of the Radon transform image is specified as the predetermined value interval for the generation of the modified Radon transform image.

7. The method of claim 1, further comprising setting, on the modification of the values of the pixels of the Radon transform image, the values lying outside the predetermined value interval to zero.

8. The method of claim 1, wherein values of pixels of the Radon transform image arranged within a specified distance from a pixel with a value outside the predetermined value interval are modified.

9. The method of claim 8, wherein the values of the pixels of the Radon transform image arranged within a specified distance from a pixel with a value outside the predetermined value interval are modified in dependence on the distance from the pixel with the value outside the predetermined value interval.

10. The method of claim 8, wherein the values of pixels of the Radon transform image arranged within a specified distance from a pixel with a value outside the predetermined value interval are set to zero.

11. The method of claim 1, wherein the low-pass filter comprises a median filter, a bilateral filter, or the median filter and the bilateral filter.

12. A method comprising:
  generating a modified three-dimensional data record, the generating of the modified three-dimensional data record comprising applying a method for improving an image quality of X-ray tomograms to a three-dimensional original data record, the three-dimensional original data record comprising a plurality of two-dimensional X-ray tomograms, the method for improving the image quality of X-ray tomograms comprising:
    generating a low-pass filtered X-ray tomogram, the generating of the low-pass filtered X-ray tomogram comprising applying a low-pass filter to a two-dimensional X-ray tomogram of the plurality of two-dimensional X-ray tomograms comprising a plurality of pixels, wherein the low-pass filter is only applied to pixels of the plurality of pixels with image values lying within a predetermined image value interval;
    generating a high-pass filtered X-ray tomogram, the generating of the high-pass filtered X-ray tomogram comprising subtracting the low-pass filtered X-ray tomogram from the two-dimensional X-ray tomogram;
    generating a Radon transform image comprising a plurality of pixels, the generating of the Radon transform image comprising calculating a Radon transform of the high-pass filtered X-ray tomogram;
    generating a modified Radon transform image, the generating of the modified Radon transform image comprising modifying values of the pixels of the Radon transform image with values lying outside a predetermined value interval;
    generating a modified high-pass filtered X-ray tomogram, the generating of the modified high-pass filtered X-ray tomogram comprising calculating an inverse Radon transform of the modified Radon transform image; and
    generating a modified X-ray tomogram, the generating of the modified X-ray tomogram comprising adding the modified high-pass filtered X-ray tomogram to the low-pass filtered X-ray tomogram.

13. An X-ray unit comprising:
  a processor configured to:
    generate a low-pass filtered X-ray tomogram, the generation of the low-pass filtered X-ray tomogram comprising application of a low-pass filter to a two-dimensional X-ray tomogram comprising a plurality of pixels, wherein the low-pass filter is only applied to pixels of the plurality of pixels with image values lying within a predetermined image value interval;
    generate a high-pass filtered X-ray tomogram, the generation of the high-pass filtered X-ray tomogram comprising subtraction of the low-pass filtered X-ray tomogram from the two-dimensional X-ray tomogram;
    generate a Radon transform image comprising a plurality of pixels, the generation of the Radon transform image comprising calculation of a Radon transform of the high-pass filtered X-ray tomogram;
    generate a modified Radon transform image, the generation of the modified Radon transform image comprising modification of values of the pixels of the Radon transform image with values lying outside a predetermined value interval;
    generate a modified high-pass filtered X-ray tomogram, the generation of the modified high-pass filtered X-ray tomogram comprising calculation of an inverse Radon transform of the modified Radon transform image; and
    generate a modified X-ray tomogram, the generation of the modified X-ray tomogram comprising addition of the modified high-pass filtered X-ray tomogram to the low-pass filtered X-ray tomogram.

14. In a non-transitory computer-readable storage medium that stores instructions executable by one or more processors to improve an image quality of X-ray tomograms, the instructions comprising:
  generating a low-pass filtered X-ray tomogram, the generating of the low-pass filtered X-ray tomogram comprising applying a low-pass filter to a two-dimensional X-ray tomogram comprising a plurality of pixels, wherein the low-pass filter is only applied to pixels of the plurality of pixels with image values lying within a predetermined image value interval;
  generating a high-pass filtered X-ray tomogram, the generating of the high-pass filtered X-ray tomogram comprising subtracting the low-pass filtered X-ray tomogram from the two-dimensional X-ray tomogram;
  generating a Radon transform image comprising a plurality of pixels, the generating of the Radon transform image comprising calculating a Radon transform of the high-pass filtered X-ray tomogram;
  generating a modified Radon transform image, the generating of the modified Radon transform image comprising modifying values of the pixels of the Radon transform image with values lying outside a predetermined value interval;
  generating a modified high-pass filtered X-ray tomogram, the generating of the modified high-pass filtered X-ray tomogram comprising calculating an inverse Radon transform of the modified Radon transform image; and generating a modified X-ray tomogram, the generating of the modified X-ray tomogram comprising adding the modified high-pass filtered X-ray tomogram to the low-pass filtered X-ray tomogram.

15. The non-transitory computer-readable storage medium of claim 14, wherein the two-dimensional X-ray tomogram is reconstructed from a plurality of two-dimensional projection images with at least partially different projection angles.

16. The non-transitory computer-readable storage medium of claim 14, wherein the predetermined image value interval is specified for a value range of soft-tissue.

17. The non-transitory computer-readable storage medium of claim 14, wherein calculating the Radon transform comprises applying an interpolation to the high-pass filtered X-ray tomogram.

18. The non-transitory computer-readable storage medium of claim 14, wherein calculating the inverse Radon transform comprises applying an interpolation to the modified Radon transform image.

* * * * *